(12) United States Patent
Johnson et al.

(10) Patent No.: US 6,544,287 B1
(45) Date of Patent: Apr. 8, 2003

(54) SOLID FILLED IMPLANTS

(76) Inventors: Gerald W. Johnson, 2525-B Potomac, Houston, TX (US) 77057; Jeffrey W. Johnson, 13934 Bay Gardens Dr., Sugarland, TX (US) 77478; Lana Lea Johnson, 2525-B Potomac, Houston, TX (US) 77057

( * ) Notice: Subject to any disclaimer, the term of this patent is extended or adjusted under 35 U.S.C. 154(b) by 0 days.

(21) Appl. No.: 09/455,852

(22) Filed: Dec. 7, 1999

Related U.S. Application Data (63) Continuation-in-part of application No. 09/210,524, filed on Dec. 11, 1998, now abandoned.

(51) Int. Cl.$^7$ .................................................. A61F 2/12
(52) U.S. Cl. .............................. 623/7; 623/8; 623/23.72
(58) Field of Search ............................. 623/8, 7, 23.75; 424/400

(56) References Cited

U.S. PATENT DOCUMENTS

| | | | | |
|---|---|---|---|---|
| 2,516,628 A | | 7/1950 | Held ............................... | 128/4 |
| 3,834,392 A | | 9/1974 | Lampman .............. | 128/303.13 |
| 4,470,160 A | | 9/1984 | Cavon ............................... | 3/36 |
| 4,643,733 A | | 2/1987 | Becker ........................... | 623/8 |
| 4,731,081 A | | 3/1988 | Tiffany et al. .................. | 623/8 |
| 4,908,029 A | | 3/1990 | Bark ............................... | 623/8 |
| 4,969,899 A | | 11/1990 | Cox ............................... | 623/8 |
| 5,029,573 A | | 7/1991 | Chow ............................. | 128/4 |
| 5,050,585 A | | 9/1991 | Takahashi ....................... | 128/4 |
| 5,125,910 A | | 6/1992 | Freitas ........................ | 604/249 |
| 5,171,269 A | | 12/1992 | Bark ............................... | 623/8 |
| 5,176,649 A | | 1/1993 | Wakabayashi ............... | 604/164 |
| 5,258,026 A | | 11/1993 | Johnson ........................... | 623/8 |
| 5,329,943 A | | 7/1994 | Johnson et al. ................ | 128/89 |
| 5,545,217 A | * | 8/1996 | Offray et al. ................... | 623/8 |
| 5,632,774 A | * | 5/1997 | Babian ............................ | 623/8 |
| 5,655,545 A | | 8/1997 | Johnson et al. ............. | 128/898 |
| 5,658,329 A | * | 8/1997 | Purkait ............................ | 623/8 |
| 5,941,909 A | * | 8/1999 | Purkait ............................ | 623/8 |
| 5,961,552 A | * | 10/1999 | Iversen et al. .................. | 623/8 |
| 6,187,044 B1 | * | 2/2001 | Eppley ............................ | 623/8 |
| 6,214,045 B1 | * | 4/2001 | Corbitt, Jr. et al. ............. | 623/8 |
| 6,083,262 A1 | * | 7/2001 | Caravel ........................... | 623/8 |

OTHER PUBLICATIONS

Smahel, Jiri and Schneider, Kurt, and Peter Donski. Bizarre Implants for Augmentation Mammaplasty: Long Term Human Reaction to Polyethylene Strips. British Journal of Surgery (1977), 30, 287–290.

* cited by examiner

*Primary Examiner*—David H. Willse
*Assistant Examiner*—Suzette J. Jackson
(74) *Attorney, Agent, or Firm*—Robert W. Strozier (57) ABSTRACT

A container for a tissue implantable solid filler material is disclosed. The filler material can be directly inserted into a cavity within the tissue or into a shell can be inserted into the cavity which either already contains the filler or has the filler added thereto during implantation. Methods for packaging the filler material are also disclosed.

14 Claims, 6 Drawing Sheets

SOLID FILLED IMPLANTS

RELATED APPLICATIONS

This application is a continuation-in-part of U.S. patent application Ser. No. 09/210,524, now abandoned filed Dec. 11, 1998.

BACKGROUND OF THE INVENTION

1. Field of the Invention

The present invention relates to implants including at least one solid or semi-solid polymeric material for use in augmentations or reconstructions of a portion of the human body. The present invention also relates to methods for making implants including at least one solid or semi-solid polymeric material and methods for using same for augmentation and reconstruction surgery.

More particularly, the present invention relates to implants including at least one solid or semi-solid polymeric material for use in augmentations or reconstructions of a portion of the human body where at least one solid or semi-solid polymeric material is inserted directly into tissue regions or inserted into expandable or non-expandable containers or shells inserted into tissue regions. The present invention also relates to methods for making implants including at least one solid or semi-solid polymeric material and methods for using same for augmentation and reconstruction surgery.

2. Description of the Related Art

Implants, especially, chin, cheek, nose, malar, pectoralis, calf, breast, buttocks, etc. implants, are usually made of soft or semi-firm/fluid silicone rubber which is then inserted into a region of the body to augment or reconstruct that region of the body. Thus, in breast augmentation surgery, a shell is inserted into a cavity either above the muscle wall or below the muscle wall. The shell is either pre-filled with a fluid or the shell is filled with fluid after insertion. Such augmentation/reconstruction implants and method for their use, implantation and filling are disclosed in the following U.S. Pat. Nos. 2,516,628, 3,834,392, 4,470,160, 4,643,733, 4,908,029, 4,969,899, 5,029,573, 5,050,585, 5,125,910, 5,176,649, 5,258,026, incorporated herein by reference.

However, all of these implant constructions revolve around the use of fluids some of which may be harmful, that are capable of leaking out of the containment devices (shells) requiring additional surgery to correct or remove. Thus, there is a need in the art for improved implants and implants methods for augmentation and reconstruction of body portions.

SUMMARY OF THE INVENTION

The present invention provides an implant including at least one solid or semi-solid polymeric material for use in augmentations or reconstructions of a portion of animals or humans, especially into tissue regions of animals or humans, where the material is inserted directly into tissue regions or inserted into expandable containers or shells inserted into tissue regions of animals or humans.

The present invention provides implants including at least one solid or semi-solid polymeric material contained in a shell for use in augmentations or reconstructions of a portion of the human or animal body.

The present invention provides implants including at least one solid or semi-solid polymeric material contained in a bio-erodible shell for use in augmentations or reconstructions of a portion of an animal including an human body.

The present invention also relates to methods for making implants according to the present invention.

The present invention further provides methods for inserting implants including at least one solid or semi-solid polymeric material into a tissue region of an animal or human.

DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that body portion augment/reconstruction implants can be constructed that do not rely on the exclusive use of fluids for maintaining implant dimensions. The present invention uses implants including at least one solid or semi-solid polymeric material in augmentation and reconstruction surgery.

The inventors have also found that the look and feel of the shell-less or bio-erodible shell implants of this invention have a more natural appearance as compared to implants contained in a non-bioerodible shell. Breast implants, as well as other implants, utilizing shells often assume a shape similar to the shape of the shell and for circular shells the implants have a more circular appearance than natural breasts. Moreover, breast implants having non-bioerodible shells tend to be painful when the recipient is laying on her/his stomach, when hugging others or generally whenever pressure is applied against the recipient's breasts where the implants reside. Furthermore, the shelled implants tend not to appear as natural as non-augmented breasts appear and often do not naturally change shape when the recipient changes positions such as when the recipient lies down on her/his back, raises her/his arms or performs other movements.

On the other hand, the shell-less implants or the bio-erosion shelled implants of the present invention improve the look, feel and movement of the augmented breast making the augmented breasts appear more natural. Thus, the shell-less or bio-erodible shelled implants of this invention have a more natural or normal contour and appearance from the shoulder to the nipple than traditional non-bioerodible shelled implants. In fact, the implants so resemble the contour of a natural breast that the general public would not readily notice the tell-tale signs that the recipient has undergone breast augmentation surgery.

The implants of the present invention can comprise the at least one solid or semi-solid polymeric material solely, i.e., the material is directly inserted in to a desired tissue region The implants of the present invention can also comprise the at least one solid or semi-solid polymeric material contained within a flexible containment device or shell. In the shell-less application, the implants do not suffer from scar tissue formation around the shell that can cause distortions of the implant in the body portion. Such distortions can be disfiguring causing initially, well-proportioned implants to undergo post-surgical contractures. Contractures are generally thought to arise when the body forms a membrane surrounding a foreign object (a scaring process). This membrane includes myofibroblast cells that can cause compressive forces to be applied to the object. If the object is deformable, then membrane hardening processes can cause contractures, disfiguring the implant and the tissue in which the implant was placed.

The implant of the present invention can be inserted into a body region by directly feeding or inserting the polymeric material into the body region. The implants of the present invention can comprise the polymeric material contained in a flexible, inflatable device or shell. The shell can either be inserted into the body region prior to filling with the polymeric material or a filled shell can be inserted into the body region.

Preferably, a cavity is formed in the desired body region prior to implantation to facilitate implant insertion. The cavity can be created using any mean known to surgeons, such as surgical dissection, tissue expansion using an inflatable balloon-type devices or the like. If an inflatable tissue dissector or expander is used, then the expander is inserted into the body region through an incision made proximal to or distance from the desired region. A tool is then used to create an initial pocket in the tissue region for insert of a deflated tissue expander device.

After the tissue expander is properly positioned in desired body region, inflation of the expander results in the formation of a cavity of a given size and shape. The cavity is then filled with the implant which is generally smaller than the cavity into which the implant is inserted. Generally, the cavity created by the tissue expander is larger than the final size of the implant. Thus, the cavity is generally about 10% to about 200% larger than the implant, preferably, between about 25% and about 150%, and particularly, between about 50% and about 100% larger than the final volume of the implant. The inventors have found that cavities between about 25% to about 75% give the best overall results post-surgery. Numerous United States Patents address and describe in greater detail tissue separation, dissection or expansion including U.S. Pat. Nos. 2,516,628, 3,834,392, 4,470,160, 4,643,733, 4,908,029, 4,969,899, 5,029,573, 5,050,585, 5,125,910, 5,176,649, 5,258,026, incorporated herein by reference. Of course, any surgical method can be used to form the cavity including, without limitation, mechanical or electrical cutting. Moreover, the incisions can be directly into the breast from any side or through a more remote site such as the naval.

The general procedure for using the implants of this invention is to first identify the body region into which the implant will eventually be inserted. If the body regions are the breasts, then the implants will result in breast augmentation surgery. Three scenarios will serve to illustrate breast augmentation using the implants of this invention. The first scenario addresses insertion of the fibrous material directly into a breast tissue.

Generally, one or more small incisions are made just below the breast line and generally positioned in the center of the breast. A surgical tool may then be inserted into the incision and an insertion pocket maybe made above the muscle layer underlying the breast. A tissue expander (an inflatable balloon of a variable size and shape and able to expand to a size equal to the desired implant size or to any reasonable size larger than the desired implant size) is inserted into the insertion pocket. The tissue expander is than filled with fluid to create a cavity having a volume equal to or greater than the final volume of the desired implant. Preferably, the cavity is made about 50% larger than the final size of the implant.

Once the expander is filled, the expander is than massaged and compressed to ensure proper formation of the cavity. If the tissue does not readily separate, then the balloon can be deflated and a putter-like tool, a hockey stick-like tool or any other tool the surgeon prefers can be used to break any connective tissue between the muscle layer and the breast layers. After breakage of the connective tissue, the expander maybe re-inserted and re-inflated, massage and compression re-done until a proper cavity to house the implant is prepared.

After cavity creation and removal of the expander, the solid or semi-solid polymeric material is simply inserted directly into the cavity using any convenient means. For fibrous material such as yarn or the like, forceps or an unwinding device, similar to a fishing reel run in reverse with a eyelet guide to direct the lay down of the yarn, can be used. If the polymeric material is short or chopped fibers, fiber balls (like cotton balls), beads, pellets, granules, powders, flakes or the like, then a fluid carrier can be used to carry the material into the cavity through the incision. The carrier fluid can escape through one or more exhaust ports either associated with the initial pocket incision or other incisions associated with the cavity. The carrier fluid can be a gas or liquid or combination thereof and the injection process is designed to retain the fill material within the cavity. Retention of the material in the cavity can be accomplished by placing a screen or screening device in the exhaust pathways to allow the fluid to exist, but not the filler material. After insertion the polymeric filler material, a small amount of sterile fluid can be injected into the cavity prior to suturing.

The second scenario involves insertion of the shell after cavity formation, i.e., a tissue expander or the shell itself has already been used to form a cavity about 50% larger than the desired implant size. If the shell is used to form the cavity, then the sterile fluid is mostly removed. If an expander was used to form the cavity, the expander is remove and a shell is inserted. Into the shell is then inserted the filler material. Material is inserted until the desired fill of the shell is achieved. The filling procedure utilizes either a manual insertion of the fibrous material into the shell or an automated filling device can be used that either lays down the fiber into the shell or uses either a fluid or gaseous carrier to insert the fibrous material into the shell. After filling with the filler material, a small amount of a sterile fluid is inserted into the shell.

The third scenario involves insertion of a shell into the cavity pre-filled with filler material and fluid.

The first scenario is the preferred scenario because direct insertion of the filler material into the cavity gives the implant a textured surface which tends to decrease post-operative contractures and greatly enhances X-ray imaging of the tissue containing the implant. Of the shell scenarios, the second scenario is preferred, because the incision size is minimized. However, each scenario has its place and usage. When directly inserting the filler into a cavity, the entry into the cavity should preferably be closed with a baseball, i.e., use a running suture similar to a baseball stitch which a water tight seal. However, it should be recognized that any suturing technique that produces as water-tight seal can be used as well. Sometimes in addition to the baseball stitch, a polymer propylene mesh such as Marlex Mesh or the like, inserted into the deep layers of the wound and sutured in place to prevent herniation of the string.

The surgical procedures for augmentation of a female breast is one preferred embodiment of the present invention and generally, involves the implantation of novel breast implants and prostheses of this invention. The method is one where an incision can be made under the breast or inside the navel or umbilicus. Any acceptable means to create a tunnel through the appropriate body tissue layers can be used; however, the preferred approach is to use an endotube. The endotube which has an obturator with a bullet shaped tip is introduced into this incision and is pushed to a position behind the breast. A tunnel or pocket is made behind the breast to receive an implant of the present invention. The obturator is removed. Verification of the tunnel's position is made by the surgeon. The preferred verification procedure is via an endoscope. The endotube is removed leaving behind a temporary tunnel leading beneath the area of the breast.

A tissue expander or hollow prosthesis is rolled up tightly, positioned inside the end of the endotube and pushed into the tunnel behind the breast. The expander or prosthesis is held in place by the hand of the surgeon on the breast and the endotube removed. The expander or prosthesis is then pumped full of saline solution to about a 50% overfill. The filling of the expander or prosthesis with saline solution, together with the manipulation and pressure by the surgeon causes the tissues behind the breast to be dissected to form a cavity which will eventually be filled by the implant. The cavity to contain the prosthesis can be made by any means of surgical dissection such as blunt dissection, sharp dissection, electrocauterize dissection, laser dissection, etc. that the surgeon is familiar with and wishes to use.

After a short time, the expander is fully deflated and removed according to one preferred embodiment of the present invention. Once the expander is removed, the surgeon fills the formed cavity with sufficient fibrous material to fill approximately 85% of the total size of the cavity. The 85% is equivalent to a 100% implant and an overfill amount of 50%, If the shell (expander or prosthesis) is to be filled with the fibrous material according to an other preferred embodiment of the present invention, then the majority of the liquid is allowed to flow out of the prosthesis, the fill tube removed and sufficient fibrous material is inserted into the prosthesis to result in a 100% volume.

A certain amount of liquid is preferably left in the prosthesis to improve the natural feel of the fibrous implants. The procedure is then repeated for the other breast. The incisions are sutured and the patient may then go directly home from the recovery room with no hospitalization required. Under certain circumstances, a dissector is used to break any connective tissue that interferes with proper expander or prosthesis filling and/or positioning. If the shell is to be semi-permeable or permeable, then after tissues expansion, the tissue expander is removed and a semi-permeable or permeable shell is inserted into the cavity and filled with the fibrous material. When using a semi-permeable or permeable shell, then the size of the filler material should be greater than the size of permeation perforations or holes so that the filler material does not leak or bleed out over time.

Suitable material out of which the containment devices or shell can be made include, without limitation, polyolefin shells, polyurethane shells, polyester shells, silicone shells, bioerodible polymers, any other acceptable polymeric materials that do not result in serious adverse immune response problems, or mixtures or combinations thereof. Preferred containment device materials are polyolefin such as polypropylene and silicones. Polypropylene is preferred because polypropylene does not tend to interfere with X-ray imaging.

Another preferred class of shells for use in the present invention are bioerodible shells. These shells are designed to allow a scar tissue capsule to form around the shell prior to bio-erosion, so that after capsule formation and bio-erosion of the shell, the filler material or portions thereof will be substantially free of entrapment by or entanglements with scar tissue or other fibrous tissue that generally forms after implantation. With the filler material freely contained in the scar capsule formed after implantation and before shell bio-erosion, subsequent removal of the filler material, if needed or desired, will be greatly facilitated.

Yet another preferred class of shells for use in the present invention are permeable shells made of a woven or non-woven mesh, perforated polymer sheet or similar construct. Of course, the filler size should be adjusted so that the smallest filler dimension (diameter or cross-sectional dimension) is greater than the diameter or dimension of the holes in the mesh or perforated sheet. The mesh or perforated sheet can be bioerodible or non-bioerodible and is designed to retain the filler so that the capsule formed after implantation surrounds the mesh and not the filler, making subsequent filler removal easier. Moreover, if the mesh is made of polypropylene, long term survival in the body has already been proven.

Additionally, the surface of the shell can be chemically, physically or physiologically modified to decrease immune responses against the presence of the shell or to inhibit, decrease or delay scar tissue formation in close proximity to the shell. Furthermore, the shell can include a bioerodible coating containing physiological agents that act to suppress immune response and scar tissue formation for some controlled period of time. Moreover, in one preferred embodiment, the shell is constructed wholly out of bioerodible material so that the scar tissues will not be directly associated or entangled with the filler material.

Suitable filler material forms or shapes include, without limitation, powders, beads, granules, balls, torus-shapes, flakes, shaped forms, fibers, filaments, mono-filaments, yarns, fabric, or the like, combinations or mixtures thereof. The forms can be solid, hollow, aerated or blown, foamed, filled (fluid, semi-solid, solid, etc.), etc. The filled forms can be filled with any material such as a sterile solution, oils, collagen, partially cross-linked vegetable oils, biodegradable fluids, fatty acids, proteins, vitamin solutions, silicone fluids, or the like, or combination or mixtures thereof. The forms can also be made of one material coated with a second material. Thus, foams can be coated with a layer of polypropylene to form bio-inert forms using foams that may be less bio-inert.

The filler materials of the present invention is preferably either solid or semi-solid at temperatures typically experienced by an animal or human body. The material should not have a melting point within about 50° C. of normal body temperature, i.e., above about 75° C. in the case of humans. However, the material can have a glass-transition temperature at or near normal body temperature so that the material will be somewhat malleable at normal body temperature. Polymers can be designed for this purpose by simply controlling the composition of the polymer and/or its molecular weight and/or molecular weight distribution of the polymer as is well-known in the art. Semi-solid materials are those that are not truly solid but do not flow as a fluid. Such materials can include partially crosslinked low molecular weight polymers such as partially cross-linked low molecular weight polypropylene, partially cross-linked copolymers of ethylene and propylene (rubber or plastic) and partially cross-linked polymers of EPDM. Of course, other polymers or mixtures of polymers can be made semi-solid as well.

Suitable solid or semi-solid filler materials include, without limitation, synthetic materials such as polyolefins, polyurethanes, polyesters, polyamides, polyimides, hydrogels, ionomers, silicones, silicon rubbers, polysiloxanes, or the like, or combinations or mixtures thereof; and natural materials such as silk, cotton, cellulose or other similar naturally derived material or combinations or mixtures thereof; or combinations or mixtures of synthetic or natural materials. Basically, any synthetic or natural material can be used provided that it does not cause serious adverse immunological responses. The polymeric material can also be polymers incorporation two or more monomers, i.e., copolymers, terpolymers, etc., graft polymers, telomers or the like.

Generally, the volume of the implant will be controlled by the total weight of the material inserted into the cavity because each material will have a given density. The density and therefore the weight of material used will, of course, change depending on the material used. Continuous yarns or yarns having a length between about 1 cm and about 1000 cm, preferably between about 10 cm and about 100 cm, are preferred in certain applications. When the filler material is beads or the like contained in a shell, then the implants will be similar to bean bags. If the material swells in water based fluids, including bodily fluids, then the volume to weight ratio must be modified by the swell ratio of the material. This applies generally to hydrogel and ionomer based materials. For a continuous yarn, the yarn should have a diameter or cross-sectional dimension between about 0.1 mm to about 3 mm, preferably between about 0.5 mm and about 2 mm and particularly between about 0.5 mm and about 1.5 mm. The inventors have found that yarn having a diameter of about 0.75 mm tends to compact and feel relatively harder to the touch than yarn of a greater diameter and have found that yarn having a diameter of between about 0.8 and about 1.2 mm have the improved feel to the touch.

Polypropylene is the preferred polymeric material. When using polypropylene yarn, the yarn is preferably washed repeatedly with an aqueous solution which can include a surgical detergent and other agents such as anti-microbial agent. These initial washing are generally accompanied by the removal of finishing oils and compounds, evidenced by foaming. After several of these washes (until no more foaming occurs) generally about 3 to about 5 washes, the polypropylene is washed repeatedly with deionized water.

Because the polypropylene yarn has a particular cross-sectional area and weight per length, the amount of yarn used in an implant will be a given length of material which can be determined by the yarn cross-sectional area and the length of yarn used. Of course, if the polypropylene is prewashed and designed specifically for augmentation surgery, then these washing steps may not be necessary.

As with the shells, the surface of the fibrous material can be chemically, physically or physiologically modified or coated to decrease immune responses against the presence of the shell or to inhibit or decrease scar tissue formation in close proximity to the shell. Furthermore, the fibrous material can include a bioerodible coating containing physiological agents that act to suppress immune response and scar tissue formation for some controlled period of time. The fibrous material can also have the bioerodible fibers co-woven with the continuous or non-continuous fibers or fabric of the present invention. One such coating is to coat the non-erodible yarn or fibrous material with a bioerodible material. This combined material is thought to facilitate implant withdrawal. The filler material can also be placed in a shell made totally of bioerodible materials. The value of this type of shell is that it would allow the body to form a fibrous membrane around the shell, but disintegration of the shell would then remove the immune stimulus and prevent or reduce the fibrous membrane from contracting and causing implant to feel hard. The body's formation of this fibrous membrane around the bioerodible shell should prevent the string or fibrous filaments from being incorporated and trapped in the tissue.

Such bioerodible polymers include, without limitation, biocompatible polymers that are preferably bioerodible by cellular action and/or are biodegradable by action of non-living body fluid components. Such polymeric substances include polyesters, polyamides, polypeptides and/or polysaccharides or the like. Non-limiting examples of suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, and copolymers, terpolymers, or higher poly-monomer polymers thereof or combinations or mixtures thereof. The preferred biodegradable polymers are all degraded by hydrolysis.

Typically, the polymers will either be surface erodible polymers such as polyanhydrides or bulk erodible polymers such as polyorthoesters. Poly(l-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-co-glycolic acid) (PLG). The co-monomer (lactide:glycolide) ratios of the poly(DL-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration.

Immune suppressor agents that can be include in the bioerodible coatings or co-woven fibers, include, without limitation, corticosteroids and anti-metabolites such as 5-fluoro-uracil or any other immune suppressor agents or agents that interfere.

Preparation of Polymeric Material for Use in Implants

The polymeric filler material, whether used with or without a shell, is preferably sterile and substantially free of chemical processing agents or other chemical agents added in small amounts to polymers during manufacturing and processing such as polymerization and spinning into yarn. If yarn is purchased from a polypropylene manufacturer in bulk, then the yarn must be disinfected, washed thoroughly and sterilized.

To disinfect the yarn, the yarn is generally washed at least once in chlorinated water at room temperature or at an elevated temperature to disinfect the yarn or kill any microorganisms that may be present in or on the yarn. Although chlorinated water is the preferred disinfectant for yarn, any other suitable disinfectant can be used as well. Suitable disinfectants include, without limitation, any reagent that includes anti-microbial agents such as fungicides, bacteriacides, or the like.

After disinfecting the yarn, the yarn is washed in water, preferably distilled water or distilled, deionized water, or in an aqueous solution containing a small amount of a surfactant or mild detergent dissolved in distilled, deionized water to remove substantially all non-polymeric impurities. Generally, washing should continued until the yarn is substantially free of processing aids or other additive such as anti-oxidants or other anti-degradants. Preferably, the disinfected yarn is washed with water or the above-mentioned aqueous solution at least once and preferably at least twice and particularly at least thrice at room temperature or at an elevated temperature or until no color or foaming is noticed in the wash solution. The detergent can be any commonly used detergent such as Tide® or the like. If a mild detergent is used, then the yarn should be washed at least once in distilled or distilled deionized water to remove any detergent residue.

Once the yarn has been disinfected and thoroughly washed so that it is substantially free of chemical spinning, finishing, flow or anti-degradation agents, the yarn is cut into set lengths which correspond to a desired volumeric equivalent and sterilized. Of coures, the yarn can be sterilized in bulk and cut subsequently, but sterile handling must be exercised. Generally, sterilization will occur at an elevated temperature and for a time sufficient to sterilize the yarn for implantation. Typically, the sterilization temperature will be between about 175° F. and about 275° F., preferably between about 185° F. and about 265° F., particularly between about 195° F. and about 255° F., and especially between about 205° F. and about 235° F. Typically, sterilization time will be between about 15 minutes and about 4 hours, preferably between about 20 minutes and about 2 hours, and particularly between about 30 minutes and about 1 hour. Generally, for small implant volumes, less than about 100 cc, a sterilization of 30 minutes at 220° F. is acceptable, while for larger implant volumes, a sterilization of 1 hour at 220° F. is acceptable.

Once sterilized, the desired length of yarn can be packaged in a sterile heat sealable bag or container and vacuum sealed. Alternatively, the yarn can be wound onto a spool either prior to or after sterilization. If the yarn is wound on the spool prior to sterilization, then the spool and the yarn can be sterilized together. The spool with the sterile yarn thereon, can then be package in sterile packaging such as a sterile bag or container and vacuum sealed. The packages can include different lengths of yarn so that the physician can select one or a number of bags to add to a desired amount of yarn to be implanted. For example, if the yarn is packaged in amount equivalent to 50 cc, 100 cc, 200 cc, 300 cc, etc., and a patient desires an implant of 350 cc, the physician could use three 100 cc bags and one 50 cc bag or any other combination to achieve the desire volumetric amount.

Alternatively, the yarn can be manufactured, washed, sterilized and packaged at the manufacturing facility. Thus, the manufacturer can process the yarn by spinning the raw polymeric material into yarn, disinfect the yarn, wash the yarn, sterilize the yarn and package the yarn in sterile packaging for shipment to physicians.

Of course, it should be recognized that other filler types such as filaments, fabric, ribbons, flakes, beads, or the like should also be subjected to the same or similar pre-implantation processing, i.e., disinfecting, washing, sterilizing and sterile packaging. Additionally, these other filler types should be pre-packaged in given amounts in a sterile container prior to use by the surgeon or other health care provider. The amount of material included in the sterile containers will depend on the shape, volume and density of the filler material. For continuous filler materials spools or other rotatable dispensing apparatus represent the preferred dispensing apparatus. For non-continuous filler materials, given amounts of the material can simply be sealed in a container such as a bag which can be vacuum packed or not. Alternatively, the non-continuous filler materials can be sealed in a container along with sterile medium such as saline to aid in dispensing the filler during implantation.

Referring to the drawings by numerals of reference, and more particularly to FIGS. 1–10C, there are shown the implantation of the implants of the present invention and the surgical instruments and methods for endoscopic breast augmentation mammoplasty. Although the invention is being described with respect to breast augmentation mammoplasty, the invention is not confined to mammoplasty, but has general applicability to tissue augmentation of other regions of the body. Moreover, even though the figures and the description that follows illustrate implants positioned above the muscle layer below the breast, the implants of the present invention can be placed either above, below or above and below the muscle layer.

Figure 1:
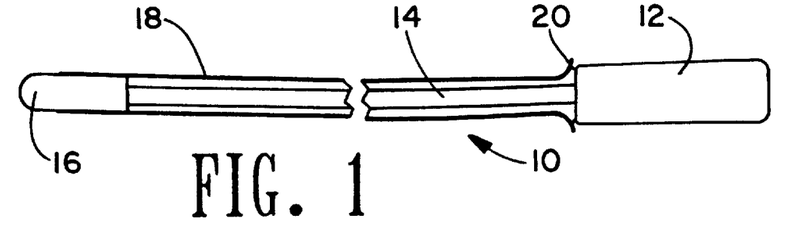
FIG. 1 is a view, partly in section, of an endotube and obturator for use in an endoscopic breast augmentation mammoplasty according to a preferred embodiment of this invention.

Referring now the FIG. 1, an obturator 10 comprises a handle 12, rod 14, and bullet-shaped nose piece 16, preferably formed of surgical stainless steel or plastic of satisfactory strength. The obturator 10 (or tracer) is shown in position fully inserted inside a hollow endotube 18 which is open at both ends and has a flared end portion 20 adjacent to handle 12. The endotube 18 is also preferably formed of surgical grade stainless or plastic of satisfactory strength steel. While surgical steel is preferred for instruments having long life, it may be desirable to make the instruments of a sterile plastic which may be disposed of after each operation.

The obturator 10 is of any convenient length including the handle 12 and the nose piece 16 sized to sliding fit inside endotube 18. The endotube 18 is generally shorter than the obturator 10 and generally has a has an I.D. of about 0.70" and O.D. of about 0.73". Smaller sizes, of course, may be used if desired. When the obturator 10 is assembled in the endotube 18, the distance from the flared end 20 to the end of the nose piece 16 is any convenient distance. The dimensions are chosen to fit the requirements of the surgery. It the incision is directed through the navel, then the length required is sufficient to extend from the navel to a point behind the breast of the surgical patient. Different lengths may be required for different sizes of patients. The diameter of the endotube and obturator are chosen to provide an opening large enough for the surgical instruments which are to be introduced through the endotube without being so large that excessive trauma is produced by the surgical procedure.

Figure 2:
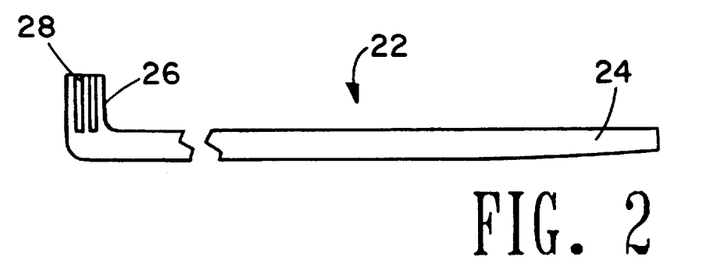
FIG. 2 is a plan view of a dissector used in separating tissue in the endoscopic breast augmentation mammoplasty according to a preferred embodiment of this invention.

In FIG. 2, there is shown a dissector 22 for blunt dissection of tissue in the procedure described below. The dissector 22 has a handle 24 at one end and bent portion 26 at the other end. The bent portion 26 has a plurality of grooves 28 cut therein with sharp edges to facilitate dissection during the surgical procedure. Generally, this tool is used only when the expander is unable to achieve adequate tissue dissection, i.e., connective tissues between the muscle layer and the breast tissue prevent adequate cavity formation.

Surgical Procedure for Endoscopic Breast Augmentation Mammoplasty

Figure 3:
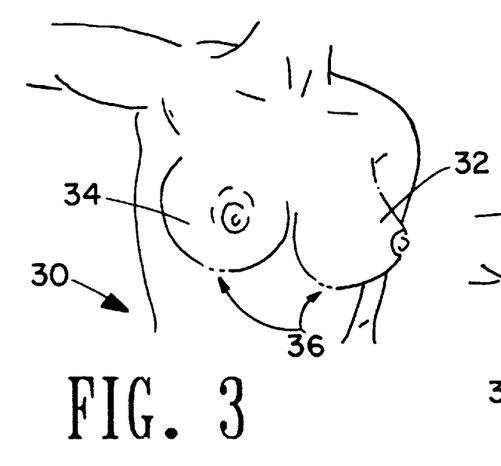
FIG. 3 is a schematic view of a female torso with markings for guidance of the surgeon in carrying out an endoscopic breast augmentation mammoplasty through a breast incision made according to a preferred embodiment of this invention.

The new implants and the surgical procedures for performing augmentation of the female breast are shown in FIGS. 3–8B were performed under general anesthesia. A female patient 30 having a right breast 32 and left breast 34 is placed on the operating table and marks 36 made in preparation for surgery as shown in FIG. 3. If the implant is to proceed through the naval, then the procedure set forth in U.S. Pat. No. 5,258,026, incorporated herein by reference, may be used.

Figure 4:
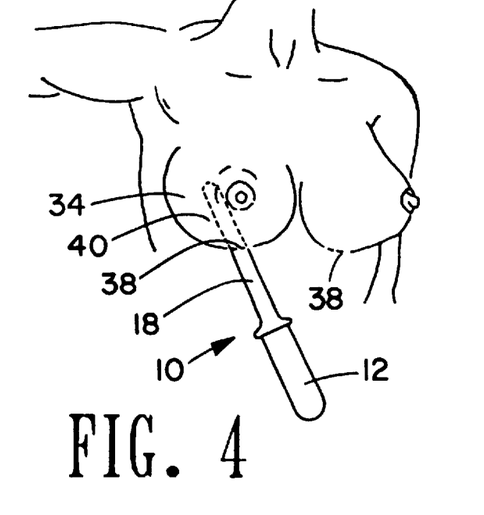
FIG. 4 is a schematic view of a female torso, as in FIG. 3, showing the endotube and obturator of FIG. 1 partially inserted in the right breast according to a preferred embodiment of this invention.
Figure 5A:
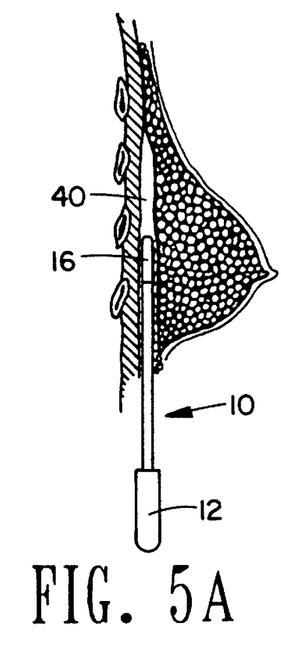
FIG. 5A is a sectional view of a female torso, including the rib cage and the breast between the breast tissue and muscle showing the endotube and obturator of FIG. 1 inserted beneath the breast to form a pocket to receive an implant shell or tissue expander according to a preferred embodiment of this invention.

Referring now to FIGS. 4 and 5A, the endotube 18 and obturator 10 with the bullet shaped nose 16 (assembled as in FIG. 1) is introduced into incisions 38 made at the marks 36 below the breast producing a space 40 behind the breast which is ultimately expanded into a pocket or cavity designed to receive a breast prosthesis or implant. As the endotube 18 (and the obturator 10) is pushed over the inferior margin of the rib cage the operator manipulates the tube 18 with one hand and the breast with the other hand to keep the tube 18 below the breast tissue, but above the pectoralis muscle fascia, if the operator wishes to place the implant in the subglandular or submammary position. If the operator wishes to place the implant submuscular, then the endotube and breast are manipulated in order to allow penetration of the pectoralis muscle fibers and direct the endotube to a submuscular position.

The obturator 10 is then removed and an endoscope is introduced to verify position of the space 40 and inspect for bleeding. If bleeding is encountered or if further cutting or cauterization is required, then a standard surgical instrument can be introduced through endotube 18 to stop bleeding or to cut or cauterize as needed. The space 40 is preferably irrigated using an irrigation tool inserted into the space 40 through endotube 18.

Figure 5B:
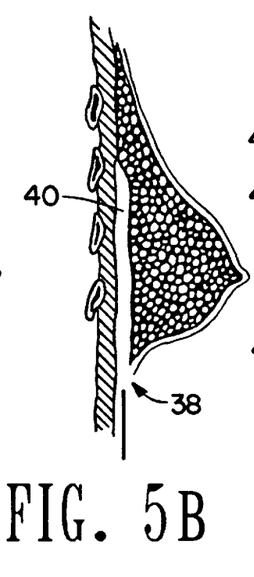
FIG. 5B is a sectional view of a female torso, including the rib cage and the breast, as in FIG. 5A, showing the endotube and obturator removed to form a pocket to receive an tissue expander or implant according to a preferred embodiment of this invention.

The endoscope and endotube 18 are then withdrawn as shown in FIG. 5B. An inflatable prosthesis, implant or tissue expander 42 is completely evacuated of air and rolled up tightly. The preferred procedure for rolling up the implant or expander 42 is to position a fill tube 44 on the implant or expander 42 at about a 6 o'clock position, and the implant or expander 42 is positioned so a valve 46 associated with the expander 42 is on the underside. From the 3 o'clock position, the one half of the implant is rolled up to the midline, then from the 9 o'clock position the other half of the implant is rolled up to the midline.

Figure 5C:
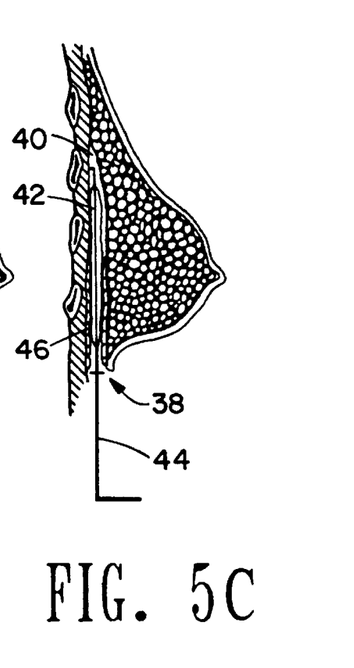
FIG. 5C is a sectional view of a female torso, including the rib cage and the breast showing the endotube and a tissue expander or implant shell carried thereon inserted beneath the breast in the pocket formed in a previous step in the procedure and showing the expander or shell fill tube extending from the end of the endotube according to a preferred embodiment of this invention.

With the implant or expander 42 tightly rolled in this fashion, the fill tube 44 of the expander 42 is then passed through the endotube 18 from the front end of the endotube, coming out the back end. The expander 42 is then partially introduced into the end of the endotube 18. At this point, the expander 42 is introduced into the space 40 beneath the breast, keeping the valve 46 of the expander 42 down (against the muscle) as shown in FIG. 5C.

Figure 6A:
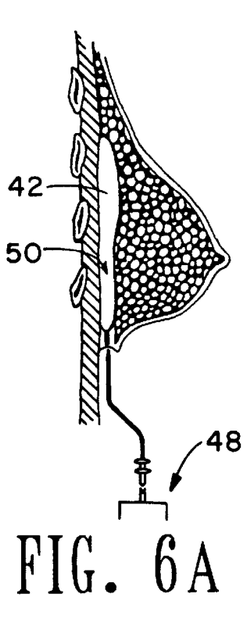
FIG. 6A is a sectional view of a female torso, including the rib cage and the breast, as in FIGS. 5A–C, showing the endotube removed and a tissue expander or shell inserted beneath the breast in the pocket formed in a previous step in the procedure and showing the expander or shell fill tube connected to a pump for filling the expander or shell according to a preferred embodiment of this invention.

Referring now to FIG. 6A, the expander 42 is held manually by the operator and by squeezing the breast, the endotube 18 is withdrawn to leave the expander in place with the fill tube 44 coming out through the incision 38. The fill tube 44 of the expander 42 is then connected to a syringe or other device 48 and the expander 42 is filled with sterile physiologic saline to form a pocket or cavity 50 for the implant.

Figure 6B:
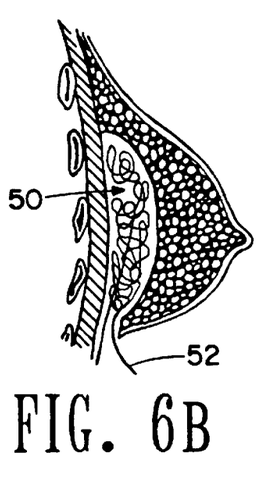
FIG. 6B is a sectional view on the female breast, as in FIG. 8, showing a cavity formed by the expander where the cavity is being filled with fibrous material according to a preferred embodiment of this invention.
Figure 6C:
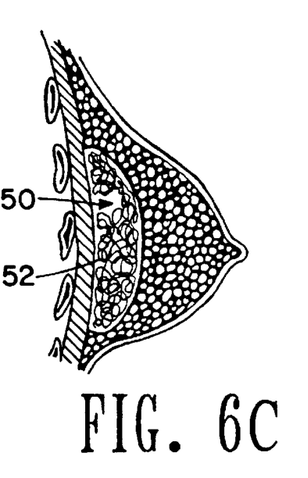
FIG. 6C is a sectional view of the female breast, as in FIG. 6B, after insertion of the desired amount of fibrous material and closure of the incision according to a preferred embodiment of this invention.
Figure 7A:
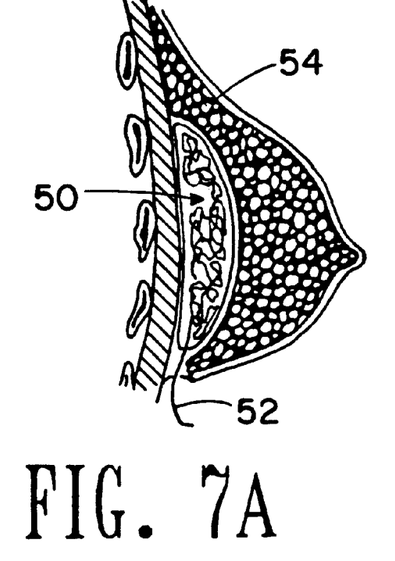
FIG. 7A is a sectional view of the female breast, as in FIG. 6A, showing fibrous material being inserted into the implant shell according to a preferred embodiment of this invention.
Figure 7B:
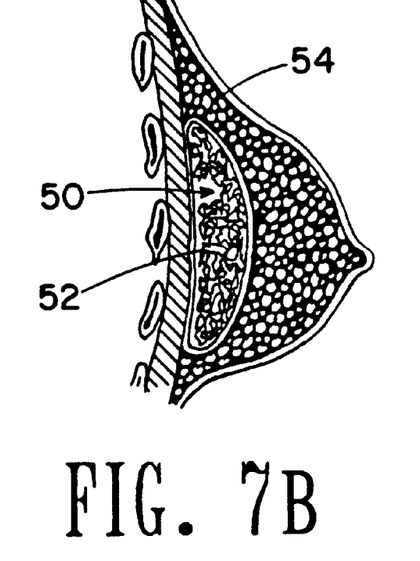
FIG. 7B is a sectional view of the female breast, as in FIG. 7A, showing the implant shell after insertion of the desired amount of fibrous material according to another preferred embodiment of this invention.
Figure 8A:
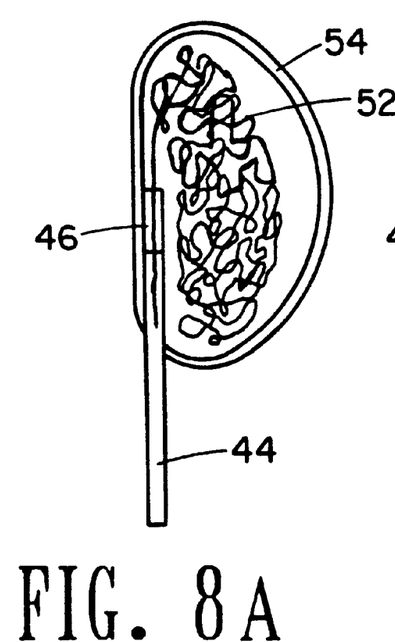
FIG. 8A is a sectional view of an implant shell as it would be positioned in a female breast, as in FIG. 7A, showing fibrous material being inserted into the shell through the shell fill tube and valve according to another preferred embodiment of this invention.
Figure 8B:
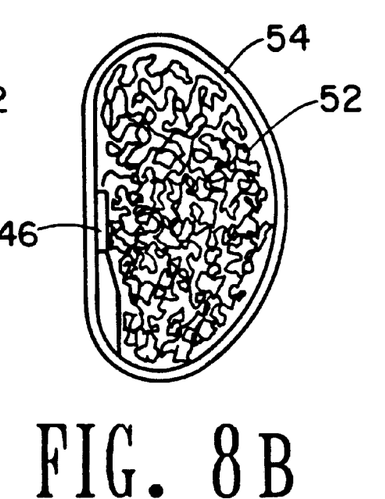
FIG. 8B is a sectional view of an implant shell as it would be positioned in a female breast, as in FIG. 7B, showing the shell after addition of the desired amount of fibrous material and closure of the shell valve and remove of the fill tube according to another preferred embodiment of this invention.

Whatever desired final implant volume, the pocket 50 is preferably oversized by a volume that is about 50% greater than the intended final implant volume. As the tissue expander or implant 42 is being inflated and over inflated, the surgeon holds and releases pressure in an appropriate manner to shape and form of the pocket 50 as it is being formed by the inflation/expansion of the expander or implant 42. After the pocket 50 is formed, the expander 42 is deflated and removed. The surgeon, then, inserts the fibrous material 52 into the pocket 50. In the case of FIGS. 6B–C, the fibrous material 52 is a continuous yarn of polypropylene having a cross-sectional dimension or diameter between 0.1 mm to about 3 mm, preferably between about 0.5 mm and about 2 mm and particularly between about 0.5 mm and about 1.5 mm. The continuous yarn 52 can be inserted by any method including the simply use of forceps. However, an automatic feed device can also be used such as an unwind reel and a eye let for directly the yarn into the pocket 50. The surgeon can then change the position of the eye so that the pocket 50 is uniformly filled. The surgeon then manipulates the breast by squeezing to uniformly distribute the fibrous material. The inventor has found that using short segments of the yarn can make removal easier. Once the desired amount of yarn is added, a small amount of sterile saline solution, generally between about 100 and 250 mL, is injected into the pocket 50 and the incisions 38 are closed.

Referring now to FIGS. 7A, 7B, 8A and 8B, a second implant 42 of the present invention is shown. The implant 42 is generally the object that made the cavity 50, but it need not be so. Once the implant 42 has be overfilled and the cavity 50 has been properly made and positioned, the surgeon fills the implant 42 with the fibrous material 52. Because in this embodiment, a shell 54 is used to contain the fibrous material, the exact form of the material is less critical, unless the shell is bioerodible. The inventor believes that a bioerodible shell will improve the ability for the fibrous material to be removed or replaced. The inventor believes that the membrane that is formed by the body to surround foreign objects would form around the bioerodible shell and when the shell erodes, the fibrous material will remain in the membrane cavity, but will not be physically associated with the membrane itself. Again, before closing the implant as small amount of sterile saline solution is injected into the implant.

The same procedure is done for the opposite breast 32. Using the endoscope, both breasts 32 and 34 are then inspected to be certain there is no pooling of saline to indicate a problem with a prosthesis and there is no excessive bleeding.

Of course, the general procedure outlined above can be used to implant an implant of the present invention into any other body region such as the chin, cheek, buttocks, lips, or other areas of the body that may need augmentation or reconstruction.

Figure 9A:
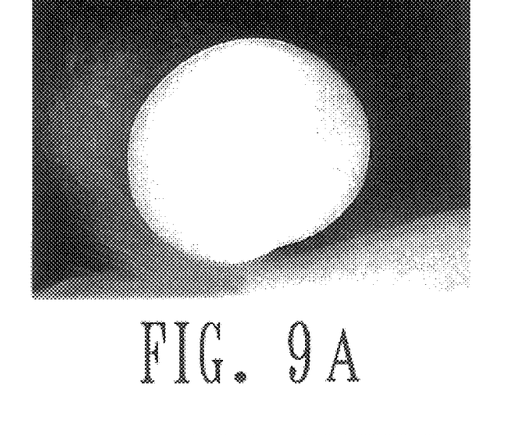
FIG. 9A is an X-Ray image of a female breast with a silicon implant positioned over the breast showing the opacity of the implant and the inability to view the breast tissue below the implant.
Figure 9B:
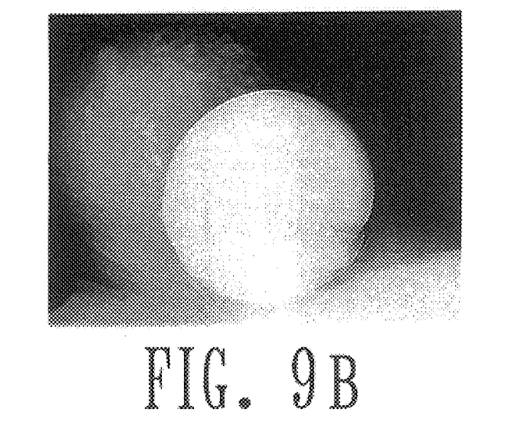
FIG. 9B is an X-Ray image of a female breast with a saline implant positioned over the breast showing the opacity of the implant and the inability to view the breast tissue below the implant.
Figure 9C:
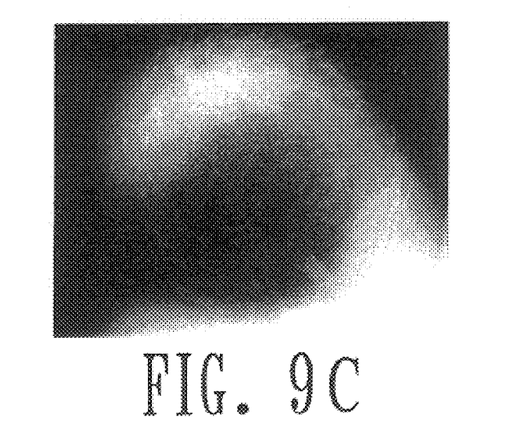
FIG. 9C is an X-Ray image of a female breast with an implant of the present invention positioned over the breast showing the transparency of such implants and the ability to view the breast tissue below the implant.

One of the significant benefits of the implant of the present invention, at least the implants that involve direct use of filler materials, is the fact that the implants do not adversely impact the ability to X-ray image the tissue bearing the implant. Referring now to FIGS. 9A–C, standard breast X-rays of a female breast are shown with different implants laid on top of the breast (not implanted). By laying the implants on the breast, the effect of the implant on X-ray imaging can be assessed. In FIG. 9A, a standard silicone breast implant has been laid on the breast. All tissues below the implant are not seen in the image. In FIG. 9B, a standard saline breast implant has been laid on the breast. Again, all tissues below the implant are not seen in the image. Finally, in FIG. 9C, an implant of the present invention (polypropylene yarn) is shown laid on the breast. Unlike the silicone or saline implants, the implant of the present invention allow the breast tissue below the implant to be see in the X-ray image.

Figure 10A:
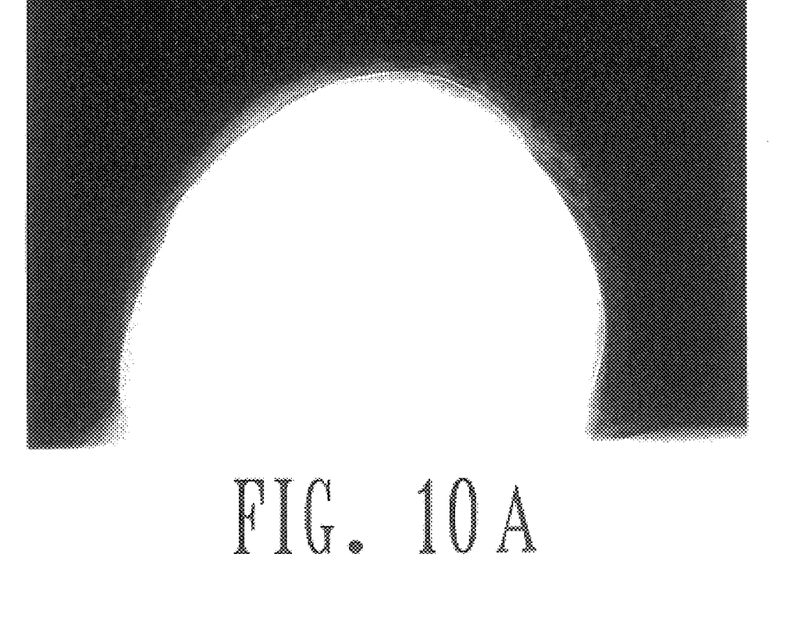
FIG. 10A is an X-Ray image of a female breast containing a silicone implant showing the inability to discern breast tissue below the implant.
Figure 10B:
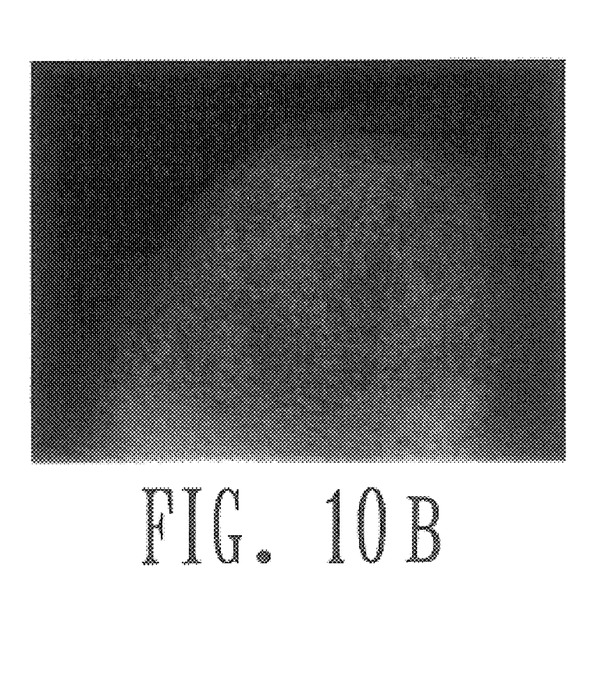
FIG. 10B is an X-Ray image of a female breast containing an implant of this invention showing the ability to discern breast tissue below the implant.

Referring now to FIGS. 10A–B, X-ray images of a female breast are shown with a silicone breast and with an implant of the present invention (polypropylene yarn). The patient is the same. The silicone implant were removed prior to implantation of the implant of present invention. Clearly, the implants of the present invention allow tissue imaging to occur without significant interference, shadowing, or hiding of surrounding breast tissue or any other tissue into which the implant is placed.

Surgical Procedure for Breast Augmentation Mammoplasty Using Bio-Erodible Shells Surgically, the procedure for breast augmentation mammoplasty using bio-erodible shelled implants in identical except for the implant itself to the procedure used in standard augmentation surgery using any other type of shelled implant. Generally, the a cavity or pocket is created in the breast, the shell is inserted and either pre-filled with the filler material or filled after implantation. If filled after implantation, then the yarn is generally feed into the implant through a tube associated with the implants value. Optionally, sterile saline solution can be added to the implant prior to closing the surgical incisions. Of course, any other surgical procedure for implanting a shelled implant can be used. Moreover, the implant can be implanted prefilled with filler and sterile saline.

Figure 11A:
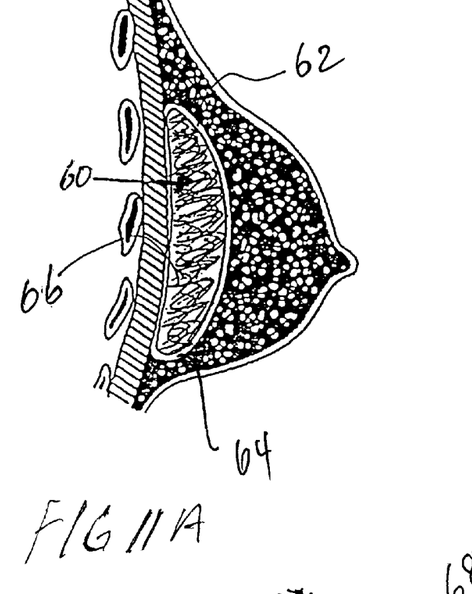
FIG. 11A depicts a breast implant including a bio-erodible shell filled with a polymeric yarn shortly after implantation.
Figure 11B:
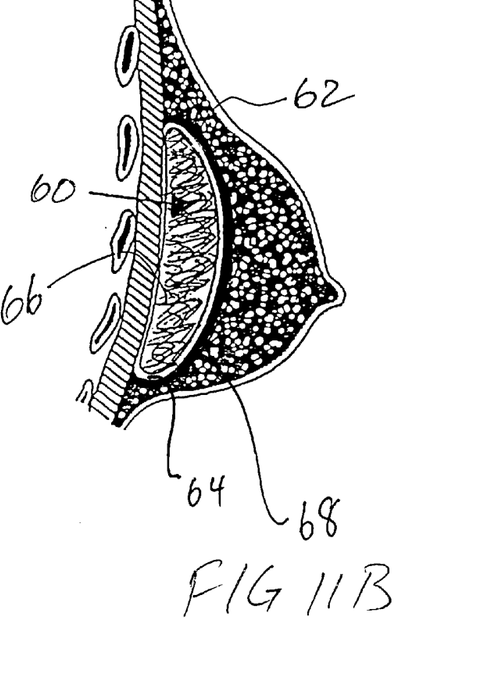
FIG. 11B depicts the implant of FIG. 11A after the formation of a scar capsule, but prior to bio-erosion of the shell.
Figure 11C:
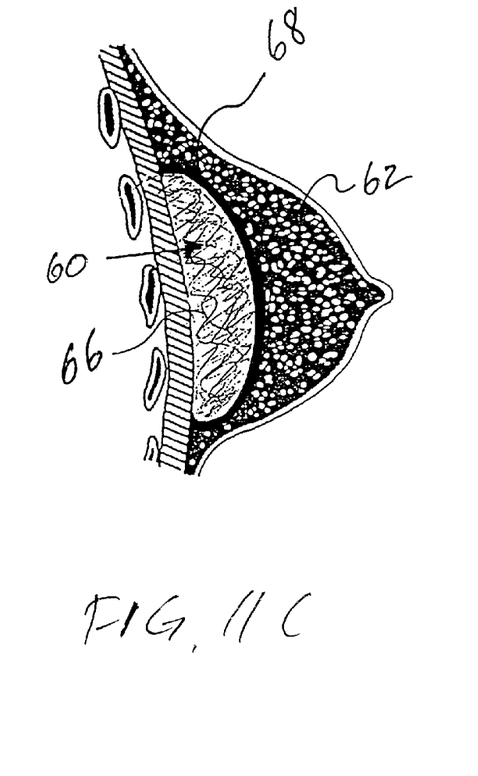
FIG. 11C depicts the implant FIG. 11A after bio-erosion of the shell.

Referring now to FIG. 11A, an implanted bio-erodible, filled shell implant of the present invention is shown generally 60 implanted in a patient's breast 62 immediately after surgery. The implant 60 includes a bio-erodible shell 64 filled with a polypropylene yarn 66. In FIG. 11B, the patient's breast forms a scar capsule 68 around the implant 60. And, finally, in FIG. 11C, the bio-erodible shell 64 erodes leaving the yarn 66 contained substantially freely within the capsule 68.

While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. An implant for tissue replacement or augmentation comprising a shell including an amount of a sterile continuous filler material, where the amount of filler material corresponds to a desired volume of the implant and where the material is a continuous yarn and the material is a polyolefin.

2. The implant of claim 1, wherein the continuous yarn is polypropylene yarn.

3. An implant for tissue replacement or augmentation comprising a shell including an amount of a sterile continuous filler material, where the amount of filler material corresponds to a desired volume of the implant and where the material is a continuous fiber, a continuous filament, a continuous mono-filament, a continuous yarn, a continuous fabric, or combinations or mixtures thereof and where the material is a synthetic material selected from the group consisting of a polyolefin, polyester, polyamide, polyimide, and combinations or mixtures thereof; a natural material selected from the group consisting of silk, cotton, cellulose, and combinations or mixtures thereof; and combinations or mixtures of the natural and synthetic materials.

4. The implant of claim 3, wherein the material includes a bioerodible outer coating and a non-bioerodible inside.

5. The implant of claim 4, wherein the inside comprises a synthetic material selected from the group consisting of a polyolefin, polyester, polyamide, polyimide, combination, and mixtures thereof; a natural material selected from the group consisting of silk, cotton, cellulose, combinations and mixtures thereof; and combinations or mixtures of the natural and synthetic materials and wherein the outer coating polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof.

6. An implant for tissue replacement or augmentation comprising an amount of a sterile, continuous implant filler material, where the amount of filler material corresponds to a desired implant volume and is implanted directly into a cavity formed in a tissue site, where the material is a continuous fiber, a continuous filament, a continuous mono-filament, a continuous yarn, a continuous fabric, or combinations or mixtures thereof and where the material is a synthetic material selected from the group consisting of a polyolefin, polyester, polyamide, polyimide, and combinations or mixtures thereof; a natural material selected from the group consisting of silk, cotton, cellulose, and combinations or mixtures thereof; and combinations or mixtures of the natural and synthetic materials.

7. The implant of claim 6, wherein the material is a continuous yarn.

8. The implant of claim 7, wherein the continuous yarn is polypropylene yarn.

9. The implant of claim 6, wherein the material includes a bioerodible outer coating and a non-bioerodible inside.

10. The implant of claim 9, wherein the inside comprises a synthetic material selected from the group consisting of a polyolefin, polyurethane, polyester, polyamide, polyimide, hydrogel, ionomer, combination, and mixtures thereof; a natural material selected from the group consisting of silk, cotton, cellulose, combinations and mixtures thereof; and combinations or mixtures of the natural and synthetic materials and wherein the outer coating polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof.

11. An implant for tissue replacement or augmentation comprising a shell including an amount of a sterile continuous filler material comprising a synthetic material selected from the group consisting of a polyolefin, polyurethane, polyester, polyamide, polyimide, hydrogel, ionomer, combination, and mixtures thereof; a natural material selected from the group consisting of silk, cotton, cellulose, combinations and mixtures thereof; and combinations or mixtures of the natural and synthetic materials, where the amount of filler material corresponds to a desired volume of the implant.

12. The implant of claim 11, wherein the material is a continuous fiber, a continuous filament, a continuous mono-filament, a continuous yarn, a continuous fabric, or combinations or mixtures thereof.

13. The implant of claim 11, wherein the material is a continuous yarn and the material is a polyolefin.

14. The implant of claim 13, wherein the continuous yarn is polypropylene yarn.

* * * * *